United States Patent
Choi et al.

(10) Patent No.: US 8,597,492 B2
(45) Date of Patent: Dec. 3, 2013

(54) NANOSCALE DNA DETECTION SYSTEM USING SPECIES-SPECIFIC AND/OR DISEASE-SPECIFIC PROBES FOR RAPID IDENTIFICATION

(75) Inventors: Wonbong Choi, Miami, FL (US); Somenath Roy, Miami, FL (US); Kalai Mathee, Miami, FL (US); Vishwanath Prasad, Denton, TX (US)

(73) Assignee: The Florida International University Board of Trustees, Miami, FL (US)

( * ) Notice: Subject to any disclaimer, the term of this patent is extended or adjusted under 35 U.S.C. 154(b) by 991 days.

(21) Appl. No.: 12/518,841

(22) PCT Filed: Jan. 30, 2008

(86) PCT No.: PCT/US2008/052422
§ 371 (c)(1),
(2), (4) Date: Dec. 15, 2009

(87) PCT Pub. No.: WO2008/094980
PCT Pub. Date: Aug. 7, 2008

(65) Prior Publication Data
US 2010/0101956 A1    Apr. 29, 2010

Related U.S. Application Data

(60) Provisional application No. 60/898,426, filed on Jan. 30, 2007.

(51) Int. Cl.
*C12Q 1/68*    (2006.01)
(52) U.S. Cl.
USPC .............. 205/792; 435/6.1; 436/94; 977/742; 977/745; 977/746
(58) Field of Classification Search
USPC ................... 204/547, 643; 205/792; 435/6.1; 436/94; 977/734, 742, 745, 746, 750
See application file for complete search history.

(56) References Cited

U.S. PATENT DOCUMENTS

| | | | |
|---|---|---|---|
| 6,518,022 B1 * | 2/2003 | Sosnowski et al. | 435/6.11 |
| 6,958,216 B2 | 10/2005 | Kelley et al. | |
| 7,857,956 B2 * | 12/2010 | Burke et al. | 204/547 |
| 2006/0063183 A1 * | 3/2006 | Segawa et al. | 435/6 |
| 2006/0246438 A1 * | 11/2006 | McCall et al. | 435/6 |

OTHER PUBLICATIONS

Nagase et al., Direct Fabrication of nano-gap electrodes by focused ion beam etching, Thin Solid Films, 2006, 499, 279-284.*
International Search Report for PCT/US2008/052422, mailed Sep. 10, 2008.
Written Opinion for PCT/US2008/052422, mailed Sep. 10, 2008.

* cited by examiner

*Primary Examiner* — J. Christopher Ball
(74) *Attorney, Agent, or Firm* — Marshall, Gerstein & Borun LLP

(57) ABSTRACT

A method and system for detecting a DNA strand using carbon nanotubes or nanowires. A specific single strand of template DNA serves as a probe for its complementary strand in a solution containing DNA segments to be tested. The single-stranded sequence-specific DNA probe segment, whose ends are modified with amine, is attached between two carbon nanotubes/nanowires. When complementary strands representing DNA segments under test are brought near the probe strands, a dielectrophoresis (DEP) field may enhance the probability of selective hybridization between the complimentary target DNA and probe DNA. A change in electrical conductance in the probe strand occurs upon hybridization of the complementary target DNA with the single probe strand. This conductance change may be measured using the two carbon nanotubes or nano-dimensional electrodes. By exploiting nano-dimensional electrodes and single strand probe DNA, the proposed system is capable of accurately detecting a single molecule of DNA.

10 Claims, 8 Drawing Sheets

NANOSCALE DNA DETECTION SYSTEM USING SPECIES-SPECIFIC AND/OR DISEASE-SPECIFIC PROBES FOR RAPID IDENTIFICATION

STATEMENT OF GOVERNMENT SUPPORT

This invention was made with U.S. Government support under Grant No. FA 9550-05-1-0232 awarded by the Air Force Office of Scientific Research (AFOSR). The U.S. Government has certain rights in the invention.

FIELD OF THE INVENTION

The present invention generally relates to a method and process of detecting DNA molecules.

BACKGROUND

The specific and quantitative detection of deoxyribonucleic acid (DNA) is of great significance in a range of applications, from disease diagnostics to the recognition of lethal bio-toxins. Recent development in nanotechnology enables us to develop new detection systems with sensitivity down to a single molecular level. Detection of single DNA hybridization event may give us the opportunity to recognize gene sequences with extremely high accuracy. In recent years, gene microarray technology has exhibited special promise due to the levels of expression of thousands of gene fragments that can be measured simultaneously. However, current gene chip technology is mainly based on fluorescence readout and requires highly precise and expensive instrumentation, limiting its use to research laboratories.

Polymerase chain reaction (PCR)-based detection of DNA markers is replacing traditional techniques such as Southerns for the presence of disease marker, or time-consuming culture methods or serological techniques for bacterial or viral detection. Discovery and development of PCR techniques has given rise to a wave of kits for various purposes that come with perishable enzyme and nucleotides with buffers and primers. Many of these components are perishable, thus limiting their shelf lives. In addition, PCR is time-consuming. Though real-time PCR machines are on the market, they are expensive and far from being portable. When kits are not available, the detection usually requires skilled personnel to configure the reactions and perform the necessary analysis with appropriate controls.

The more recent fluorescent-based techniques such as fluorescent in situ hybridization (FISH), immunohistochemical stain (HercepTest), chromogenic in situ hybridization (CISH), single-molecule photon based detection and quantum dot-mediated two-color fluorescence coincidence detection still require skilled personnel, and expensive equipment and supplies. Use of these tools is limited to select individuals and/or organizations with access to sophisticated laboratories.

SUMMARY OF THE INVENTION

A method and system for detecting a DNA strand using carbon nanotubes or nanowires. A specific single strand of template DNA serves as a probe for its complementary strand in a solution containing DNA segments to be tested. The single-stranded sequence-specific DNA probe segment, whose ends are modified with amine, is attached between two carbon nanotubes/nanowires. When complementary strands representing DNA segments under test are brought near the probe strands, a dielectrophoresis (DEP) field may enhance the probability of selective hybridization between the complimentary target DNA and probe DNA. A change in electrical conductance in the probe strand occurs upon hybridization of the complementary target DNA with the single probe strand. This conductance change may be measured using the two carbon nanotubes or nano-dimensional electrodes. By exploiting nano-dimensional electrodes and single strand probe DNA, the proposed system is capable of accurately detecting a single molecule of DNA.

DETAILED DESCRIPTION

Figure 1A:
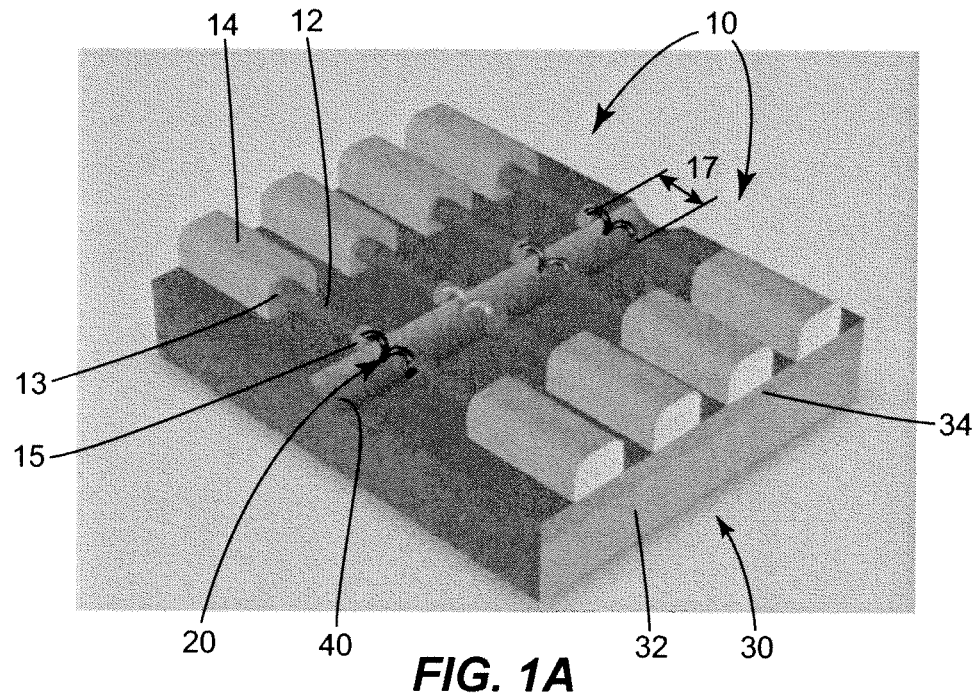
FIG. 1A illustrates a schematic of the DNA detection platform where each pair of CNT electrodes is connected to a single stranded DNA (ssDNA) probe with a distinct base sequence.

FIG. 1A illustrates a schematic of the DNA detection array assembled in accordance with the teachings of an example of the present invention, where a pair of carbon nanotube (CNT) electrodes 10 is connected to a single stranded DNA (ssDNA) probe 20 with a distinct base sequence. FIG. 1A illustrates that each electrode 10 includes a carbon nanotube 12 that is terminated at a first end 13 by a terminal 14. The ssDNA probe 20 is coupled at a second end 15 of the carbon nanotube 12. Thus, the ssDNA probe 20 is disposed in a gap 17 between second ends of two carbon nanotubes 12. In the embodiment illustrated in FIG. 1A, the electrodes 10 are disposed on a silicon chip 30 having a silicon layer 32 and a silicon dioxide ($SiO^2$) substrate layer 34. Between the second ends of each pair of carbon nanotube portions 12 is a trench 40 in the substrate layer 34. As illustrated in FIG. 1A, the ssDNA probe 20 is suspended by the second ends of the carbon nanotubes 12 over the trench 40.

Figure 1B:
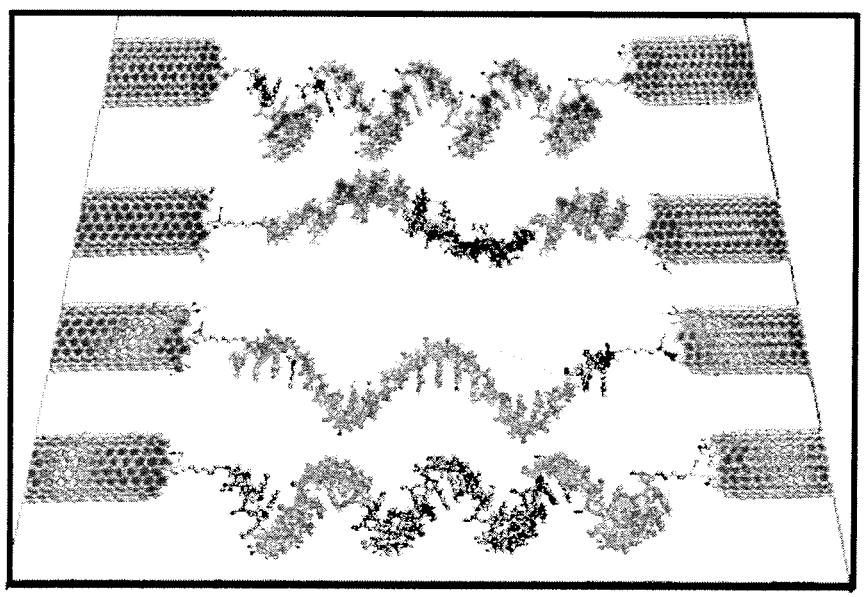
FIG. 1B illustrates a molecular diagram representing the proposed nanoelectrode array where each pair of carbon nanotube (CNT) electrodes is connected to an ssDNA probe.

FIG. 1B illustrates a molecular diagram representing the proposed carbon nanotube electrodes or nanoelectrodes and attached ssDNA probe. The operation principle lies in the fact that a template single-stranded DNA (ssDNA), electronically coupled to the nanoelectrodes, can hybridize with its complementary strand (cDNA) with extremely high specificity, and, once hybridized, results in a significant change in charge transport through the assembly. A pair of ultra-miniaturized single-walled carbon nanotube (SWCNT) electrodes 10 for controlled manipulation of a single DNA probe molecule increases the hybridization probability of the probe by applying a dielectrophoretic force on the DNA probe molecule.

Optimized operation of the detection system relies on the sensitivity of DNA-mediated charge transport to its base-pair stacking. Since ssDNA has a considerable amount of structural freedom, the stacking in such a molecule should not promote electrical conductivity in its native form. In other words, the ssDNA probe, absent other factors, should not have a high conductance. Instead, the substantially more rigid, double-stranded DNA molecule formed from the combination or hybridization of two single strands (e.g., the probe and its complimentary strand) are capable of conducting electricity more efficiently. Thus, if an ssDNA molecule is used as a molecular conduit between two nano-contacts (such as the nano-tubes of the present application), ideally no conductivity would be measurable unless a complementary strand of DNA hybridizes to the single strand to form a conductive duplex. Since only complete hybridization with a complimentary strand results in electrical conductivity, the single strand of DNA that is inserted between two CNT electrodes forms an extremely sensitive and highly selective electronic probe. Moreover, the selection of a pair of chemically functionalized SWCNT electrodes 10 having a particular diameter may enhance the specificity of anchoring only a single template DNA molecule. For DNA molecules, SWCNT electrodes having a diameter of about 1.5 nm may be appropriate.

Each nanoelectrode pair 10 in the present system may be fabricated in the following manner. First, a solution containing carbon nanotubes may be dispersed on a photolithographically patterned silicon chip having a silicon dioxide (SiO2) surface layer 34 (500 nm) using spin-coating method. The pattern on the silicon chip 30 may designed to catch and position a corresponding (e.g., matching in shape and size to the pattern) carbon nanotube(s) from the solution on to the chip. After identifying the location of an individual SWCNT on the chip, electrical connection terminals may be formed on the ends of the SWCNT for connection to other electric circuitry (to be discussed further below). The electrical connection terminals may be composed of Ti (10 nm)/Au (100 nm) and fabricated by high resolution electron beam (e-beam) lithography and a lift-off process. The ohmic contact between an SWCNT and the electrical interconnect may be formed by rapid thermal annealing (RTA) at 700 degrees Celsius for 30 seconds in high purity $N^2$ atmosphere.

A nanoelectrode pair 10 may be fabricated from the one SWCNT by creating a controlled nanogap 17 in the middle of the one SWCNT using focused ion-beam (FIB) etching. In one embodiment, the FIB etching may be performed at a central portion of the SWCNT using a Ga ion beam with a current of 3.6 pA and an accelerating voltage of 30 kV. A trench 40 beneath and between the ends of the two nanoelectrodes may be formed on the $SiO^2$ layer during ion beam etching. The width of the trench or channel may be controlled by modulating the diameter of ion beam and/or the exposure time.

Figure 1C:
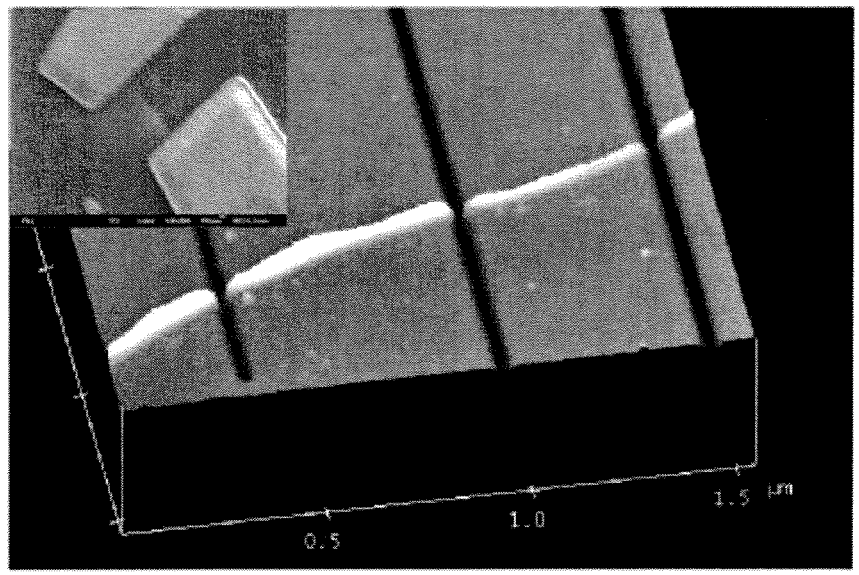
FIG. 1C illustrates a controlled dissection process of a single-walled carbon nanotube (SWCNT) SWCNT via focused ion-beam (FIB) etching (trench width ranges from 20-30 nm) with an inset picture showing an SEM image of a typical device, consisting of a pair of FIB-cut SWCNT electrodes and Ti/Au electrical contact terminals.

FIG. 1C illustrates a controlled dissection process of SWCNT via FIB etching (with trench width ranges from 20-30 nm). The top left inset of FIG. 1C illustrates a scanning electron microscope (SEM) image of a typical device, consisting of a pair of FIB-cut SWCNT electrodes and Ti/Au electrical contact terminals. In the embodiment illustrated in FIG. 1C, an 80 base-pair long DNA fragment (that is roughly 27 nm in its native form) is used with a fabricated trench of compatible dimension between the sharply cut edges of the nanotubes.

Figure 1D:
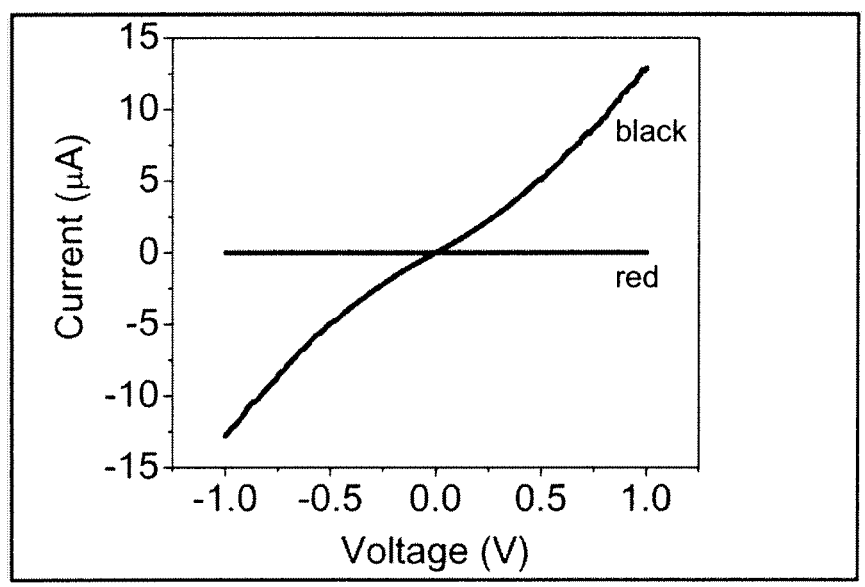
FIG. 1D illustrates an I-V characteristic graph of the SWCNT before (black line) and after FIB etching (red line)

FIG. 1D illustrates an I-V characteristic graph of the SWCNT before (black line) and after FIB etching (red line). As illustrated in FIG. 1D, there is no electrical conductivity observed between the nanoelectrodes after FIB etching. The resultant structure, in which the edges of two SWCNTs may be suspended at a separation of 27 (±2) nm, precludes the effect of substrate on conductivity when there is charge transport through a DNA molecule anchored between the SWCNT electrodes.

It has been demonstrated that interaction between DNA molecules and substrate is a key parameter that determines the conducting or insulating behavior of DNA molecules. For example, when a DNA molecule is in close contact with silicon oxide surface, the interaction between the molecule and the surface is very strong, which induces a very large compression deformation of deposited DNA. The thickness of such compressed DNA is 2-4 times lower than the diameter (about 2 nm) of its native conformation. Thus, the suspended architecture of the present application provides a more efficient system, where there is reduced interaction of the anchored DNA molecule with the $SiO^2$ surface, and hence reduced perturbation to the charge transport due to the substrate.

Figure 2A:
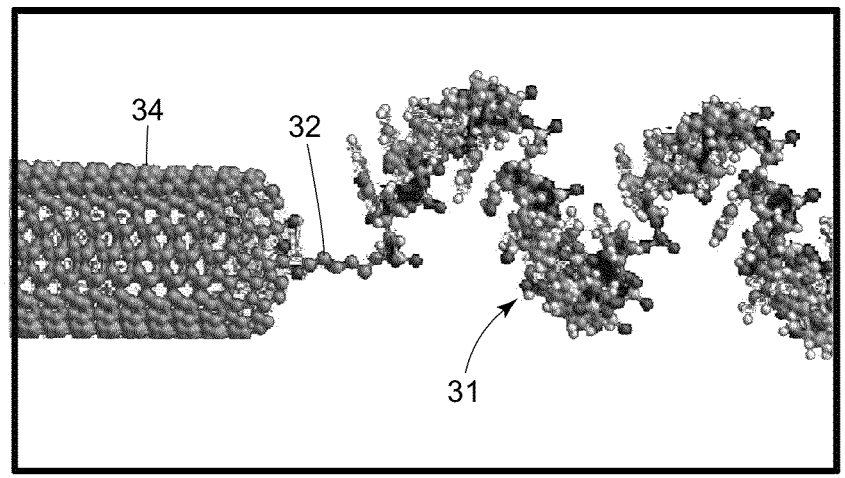
FIG. 2A illustrates a molecular diagram highlighting the attachment of an amine-terminated oligo-probe to the carboxyl terminated end of a SWCNT electrode.

The attachment of ssDNA probes to the carbon nanoelectrodes may be accomplished as follows. An efficient molecular bridge may be obtained by treating the edges of the FIB-cut nanotubes with 60% $HNO^3$ for 40 minutes to introduce carboxyl groups (—COOH), followed by several washes with deionized water to neutralize the pH. The terminal carboxyl groups may be reacted with primary amine compounds, which results in coupling the amine compound to the nanotube through an amide bond. In an application embodiment using 80-base template ssDNA strands, the strands may be customized by terminating the strands with appropriate amino modifiers at both the 5' and 3' ends. Amino modifier C6, which has a primary amino group at the end of a six-carbon spacer, may be used for 5' labeling; whereas the 3' end may be modified with amino modifier C7 CPG that contains a branched seven-carbon spacer. Amino group ended single-stranded DNA (NH2-ssDNA) probe may be linked to the SWCNT-COOH terminals by using 1-ethyl-3-(3-dimethylaminopropyl) carbodiimide (EDAC), a widely used water-soluble carbodiimide, which causes crosslinking between amine and carboxylic acid groups (FIG. 2A). FIG. 2A illustrates a molecular diagram highlighting the attachment of an amine-terminated oligo-probe 31 to the carboxyl terminated end 32 of a SWCNT electrode 34. The charge transport through the single DNA nanowire is largely influenced by the stability of the amide bonds coupling the DNA molecule to the SWCNT electrodes.

The ssDNA molecules may then be attached between the SWCNT electrodes by covalent bonding. In order to align and stretch the DNA molecule between two SWCNTs, a drop of 2 µL of 10 nM ssDNA suspension (in 1 mM sodium acetate buffer, pH 7.0) may be placed on top of the functionalized SWCNT electrodes, while applying dielectrophoresis (DEP) using an alternating current (AC).

Figure 2B:
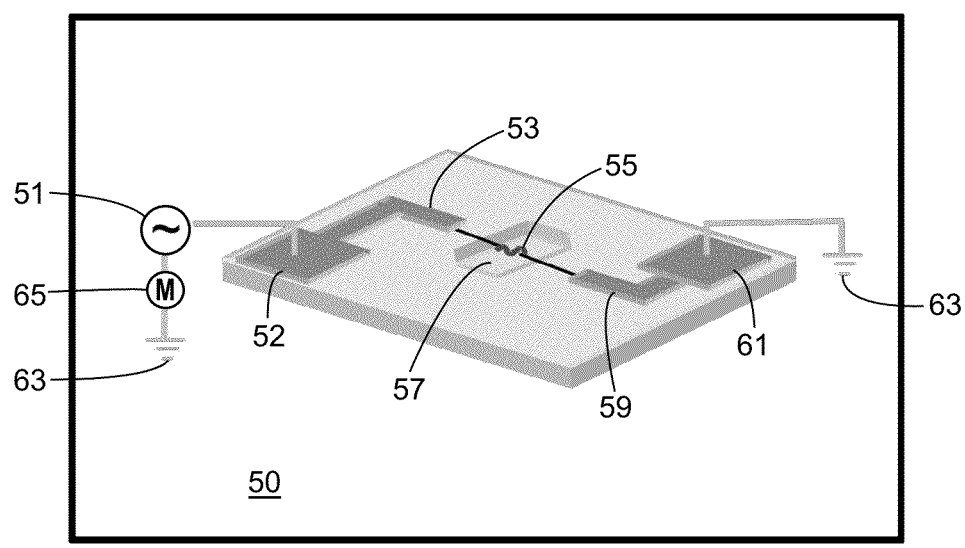
FIG. 2B illustrates a schematic of a dielectrophoresis (DEP) set-up.

FIG. 2B illustrates a schematic of the dielectrophoresis (DEP) set-up. FIG. 2B illustrates a series electric circuit 50 connecting a power source 51, a first terminal 52 of a first carbon nanotube 53, a ssDNA probe 55 disposed in a trench 57, and a second carbon nanotube 59 having a second terminal 61, where the power source 51 and second terminal 61 are connected via ground 63. The power source 51 may apply a potential across the terminals 52, 61 of the nanotubes 53, 59. In one embodiment, the power source 51 may provide a voltage or potential of magnitude 1 Vpp (corresponding to an electric field of ~40V/µm) and a 1 MHz frequency between the nanoelectrodes 10. Ideally, the nanoelectrode will apply the voltage directly to the ssDNA probe 20 (suspended over the trench 40) via the carbon nanotubes 53, 59. The application of a high frequency bias may diminishelectrochemical effects by lowering the potential drop at the electrode-solution interface. In addition to or in place of the power source 51, a conductance meter 65 may be connected in series with the other components of electric circuit 50.

Figure 2C:
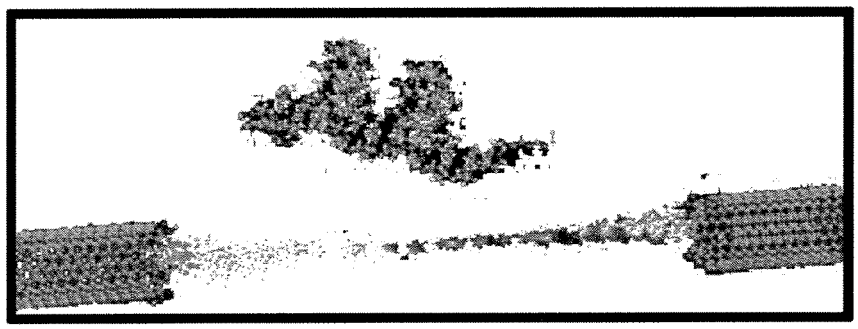
FIG. 2C illustrates a DEP force applied between a pair of SWCNT electrodes.
Figure 2D:
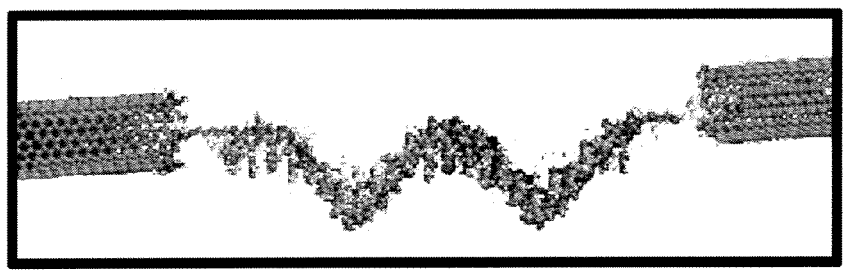
FIG. 2D illustrates the effect of DEP where the coiled DNA strand is stretched and positioned between the nanoelectrodes separated by a trench of 27±2 nm.
Figure 2E:
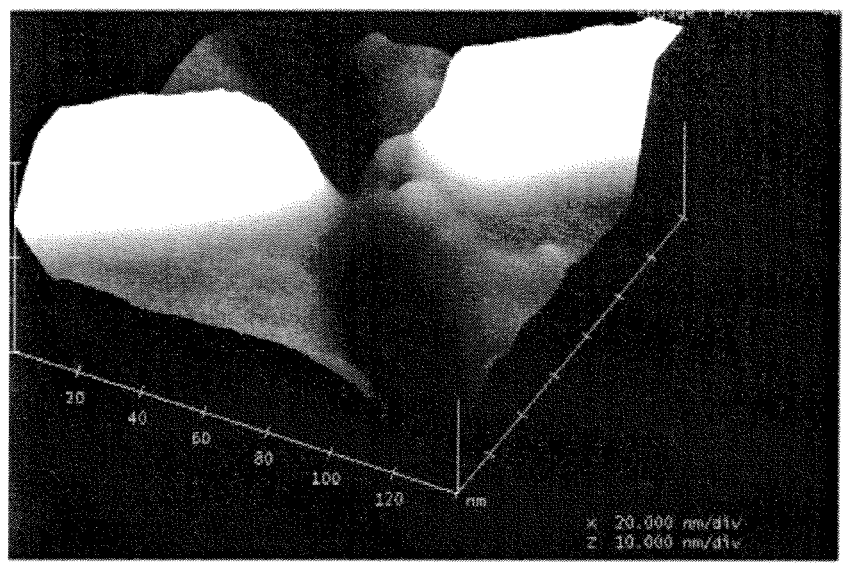
FIG. 2E illustrates a high resolution AFM image of anchored an ssDNA template strand between SWCNT electrodes.

Manipulation of a single DNA molecule is based on the interaction of the induced dipole moment in DNA with the applied electric field. When placed in solution and exposed to a non-uniform electric field (e.g., a dielectrophoretic field), a DNA molecule experiences two effects; one is a torque that aligns the molecule with the field and the other is a DEP force which drives the DNA in the direction where the electric field may be strongest. FIG. 2C illustrates a DEP force applied between a pair of SWCNT electrodes. FIG. 2D illustrates the effect of applying the DEP on a coiled strand of DNA, where the coiled DNA strand is stretched and positioned between the nanoelectrodes separated by a trench of 27±2 nm (in native form, the length of an 80-bp DNA molecule is ~27 nm). FIG. 2E illustrates a high resolution AFM image of the anchored ssDNA template strand between the SWCNT electrodes.

Figure 3A:
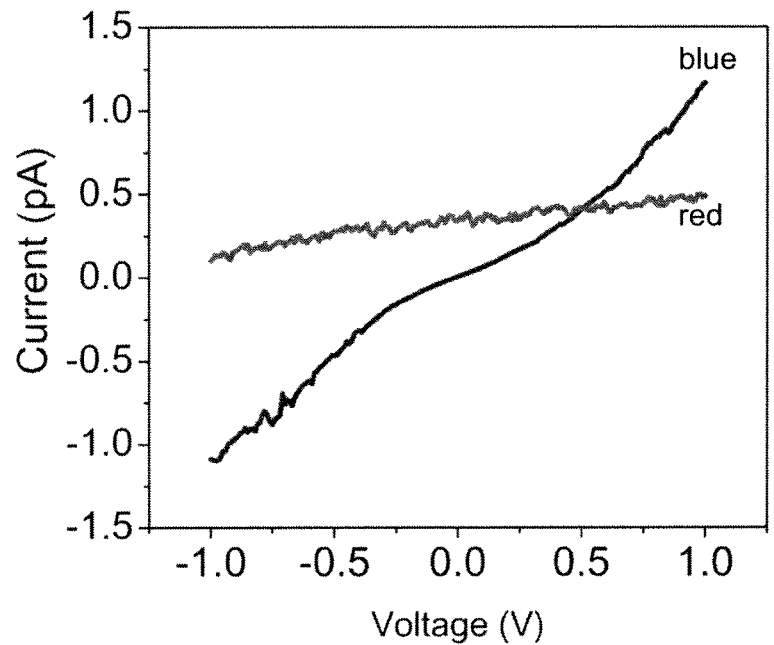
FIG. 3A illustrates current transport through a single ssDNA (blue line) and data for the control experiment in which no DNA is in the buffer solution (redline)

In one preferred embodiment, a DNA solution (e.g., containing complementary DNA to the ssDNA probe) with a concentration of 10 nM may be dropped onto one sample of nanoelectrodes connecting the ssDNA probes. A control sample of buffer solution without DNA may be placed onto a similar set of nanoelectrodes. A DEP bias of 1 Vpp at 1 MHz may be applied to both samples. The DNA containing sample as well as the control may be dried in air while the voltage continues to be applied. FIG. 3A illustrates current transport I-V data for the ssDNA with DNA solution (blue line) and for the control experiment with only buffer solution (red line). The blue line illustrates that current indeed flows through the ssDNA nanotube structure when complimentary DNA is present, whereas the redline shows little conductivity when a buffer solution containing no DNA is used. With the formation of amide bonds between both ends of the ssDNA molecules and the use of functionalized SWCNT edges, a conducting molecular bridge is established between the nanoelectrodes.

Based on the above described process, a solution of single stranded DNA may be tested for a strands containing a complimentary gene sequence to an ssDNA probe in the following manner. Conductance of an ssDNA may be measured before test solution is applied. Then, a test solution containing unknown sequences of single-stranded DNA may then be applied to the nanoelectrode-ssDNA apparatus. After the solution is applied, a bias (e.g., 1 Vpp at MHz) may be applied to the nanoelectrodes to induce a DEP field between the nanoelectrodes. The bias may be applied for a period of time necessary to induce hybridization of the ssDNA with complementary strands in the test solution, if any complimentary strands exist. A period of about 5 minutes may be sufficient to induce a detectable level of hybridization. After the test solution is applied, a conductance meter may be connected to the nanoelectrodes to determine conductance between the nanotelectrodes. If any complementary strand exists in the test solution, the complimentary strand may hybridize with the ssDNA. When hybridization occurs, the conductance between the nanoelectrodes may increase. Thus, if the conductance measured after application of the test solution is higher than the conductance before application of the test solution, then the test solution may contain strands of DNA having complementary gene sequences to the ssDNA. In one embodiment, the threshold may be set in a range of about 10-15 pA, as further discussed below.

It should be noted that water molecule distribution along the strands may affect conductivity. For example, it is speculated that the observed charge transport may be affected by a strong perturbation of the electronic system mediated by the dissipative water environment. This speculation is in agreement with the observation that relative humidity may strongly influence measured conductivity of an assembly of DNA molecules. For example, hydronium ions, $H3O^+$, are considered to be the dominant charge carriers at low water concentration (below about one monolayer) while conduction is thought to be governed by protons (supplied by the dissociation of $H^2O$ to $H^+$ and $OH^-$) at higher water concentration. While there may be a dominance of current flow through the water layer adsorbed at the backbone of single-strand as well as duplex DNA, because reduction-oxidation processes are insignificant due to relatively low voltages used in our experiments, buffer salts and the counter-ions are less likely to contribute to the total steady-state dc current. Instead, diffusion of the ions to the nanoelectrodes, especially in a moist environment, may cause extra capacitance and hysteresis, which were observed for higher concentration of the buffer solution ($\geq 10$ mM). Another possibility of charge transport through the single DNA strand is due to the hole doping of the sugar-phosphate backbone, since the energy gap between the phosphate and the counter-ion levels is very small ($\sim k_B T$). However, the conduction through the ssDNA backbone is less a factor because of the insulating sugar separating phosphate groups from each other.

Figure 3B:
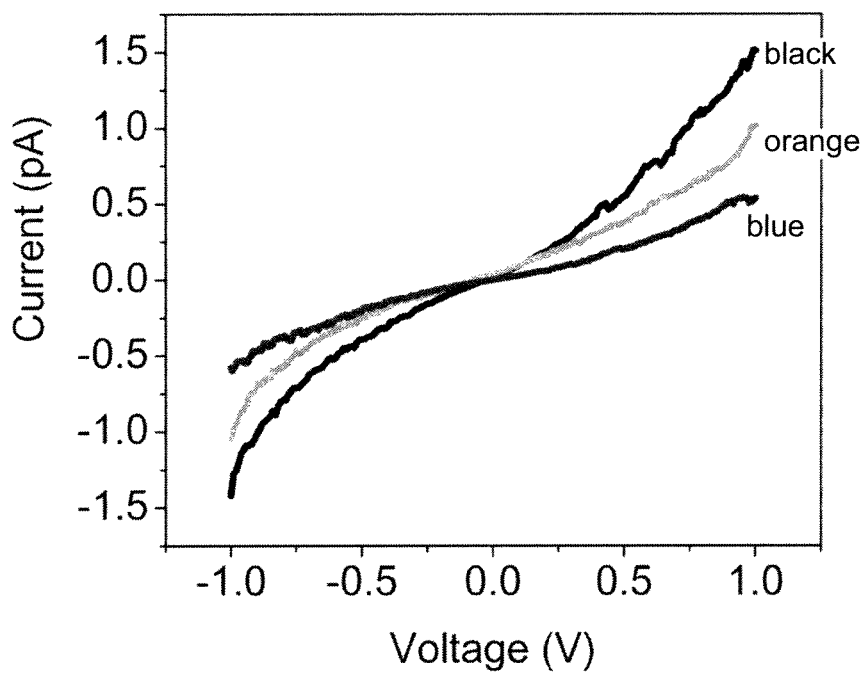
FIG. 3B illustrates current flow through a single ssDNA molecule with varying thickness of native solvent layer.

The effect of the hydration layer surrounding the single DNA strand on the electrical conductivity may be determined by measuring current-voltage characteristics through a single ssDNA molecule with different thicknesses of native solvent layer. FIG. 3B illustrates current flow through a single ssDNA molecule with varying thickness of native solvent layer (using 1 mM sodium acetate buffer, pH 7.0) caused by evaporation. The black line represents a control situation in which a control amount of solvent is applied to the array of ssDNA strand(s) and nanotubes. The orange line represents subjecting a similar array to a $10^{-1}$ Torr vacuum. The blue line represents subjecting an array for 24 hours to a $10^{-5}$ Torr vacuum and taking measurements under the same vacuum condition. FIG. 3B illustrates that with an increase in vacuum, and consequent reduction in thickness of solvent as the water molecules evaporate, that the conductivity decreases.

Figure 3C:
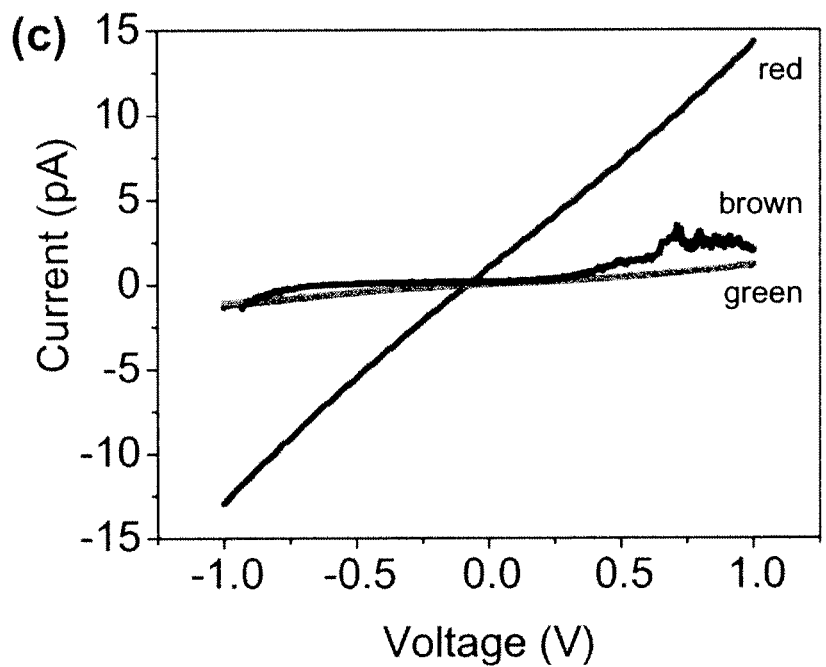
FIG. 3C illustrates electrical characteristics of the template strand and its complementary strand in buffer solution.
Figure 3D:
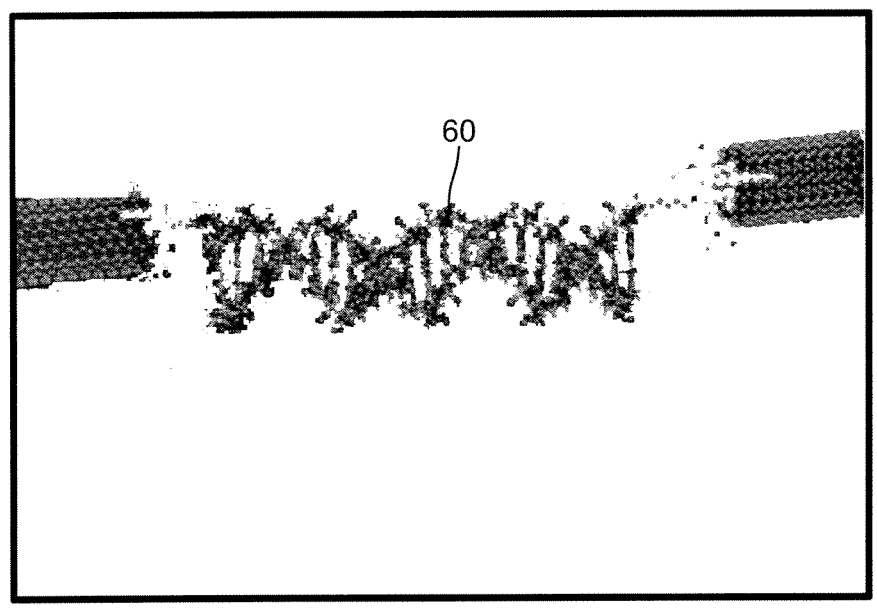
FIG. 3D illustrates a DNA duplex as a conductive nanowire where the base-pair stacking, with the restoration of conformation after hybridization of the ssDNA probe with is complementary strand, is responsible for a significant change in current transport through the assembly.

FIG. 3C illustrates further electrical characteristics of the template strand and its complementary strand in buffer solution. In particular, FIG. 3C illustrates the electrical characteristics of an embodiment of the detection method in which 2 μl droplet of 10 nM cDNA solution (in 5 mM sodium acetate buffer, pH 7.0) is placed on the detection array in the presence of an AC voltage bias with frequency 1 MHz and amplitude 1 V. The green line illustrates that the template strand alone does not conduct much electricity. When the solution of complimentary DNA is included, conductance increases (red line). When non-complementary DNA is introduced, there is no appreciable change in current signal (brown line, approx. equal to green line). The application of DEP enhances hybridization probability in a dilute solution of DNA by bringing the complementary strand in close proximity of the template/probe strand and aligning it along the field direction. It is noted that DEP may be an efficient way of overcoming the dominant Brownian motion at the nanoscale. Moreover, the throughput of the DEP-enforced hybridization process may be significantly higher than the conventional incubation because of the reduction of hybridization time from several hours down to a few minutes. After inducing the hybridization event under a DEP field for about 5 min, the sensor chips may be washed with the same buffer solution. This process may not only diminish the non-specific binding probability of cDNA, but may also ensure that the observed modulations of electrical conductance are not related to random changes in mobile charge concentrations on the device surface. It should be noted that the presence of salts in the cDNA solution may be needed to facilitate the hybridization. As delineated in FIG. 3C, the current level flowing between the pair of nanoelectrodes increases after the hybridization event takes place by an order of magnitude. As mentioned before, when only ssDNA is anchored between the SWCNT electrodes, the magnitude of current lies between 0.5 pA and 2 pA at an applied bias of 1 V, for various devices. However, for the DNA duplex the device current reaches a value anywhere between 10-15 pA. FIG. 3D illustrates a DNA duplex 60 as a conductive nanowire where the base-pair stacking (with the restoration of conformation after hybridization of the ssDNA probe with is complementary strand) is responsible for a significant change in current transport through the assembly.

In order to ensure that the observed enhancement in electrical current is only due to the DNA hybridization, several control experiments may be performed in which a drop of sterile water or phosphate buffer solution without any DNA is placed onto the array under AC biasing condition. An 80-bp DNA sequence of the model gene may be chosen for the experiments having 34 guanine-cytosine (G-C) pairs that are randomly distributed along the length of the molecule. Because of the low ionization potential associated with G-base, it causes localization of holes and the charge transport is facilitated through the hopping mechanism. Thermal hopping is expectedly more dominant over coherent tunneling mechanism of charge transport through an 80 bp long DNA duplex. In order to verify the specificity of the sensor, a droplet of test solution containing only non-complementary strand may be placed on the template DNA under identical bias conditions from a control array.

Figure 4:
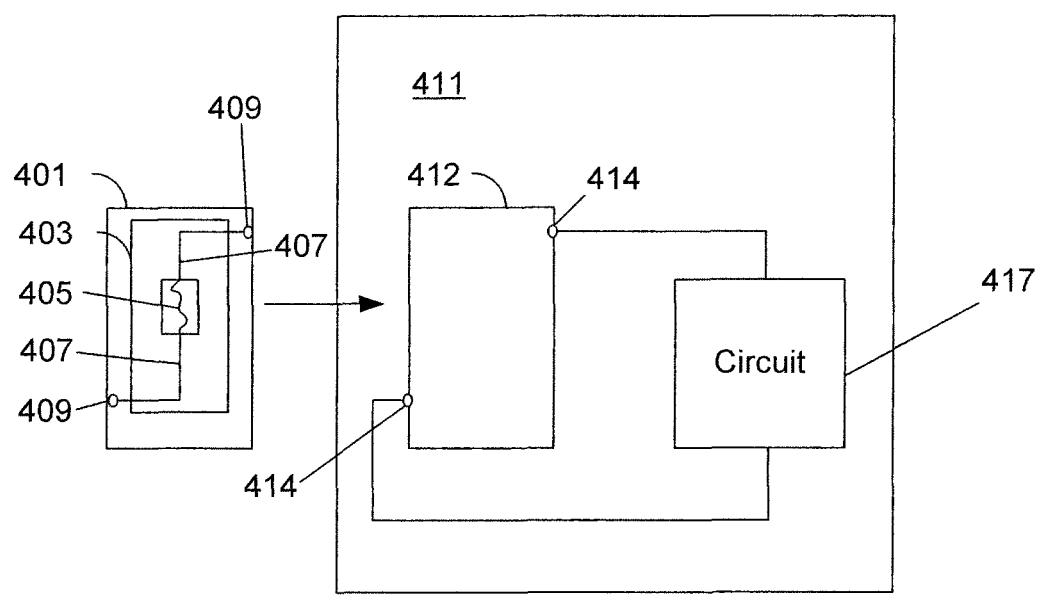
FIG. 4 illustrates a card embodiment for detecting a single stranded DNA molecule.

FIG. 4 illustrates another embodiment of a single stranded DNA detection system. The detection probe described above may be formed on a portion of a card 401 representing a substrate layer 403, such as $SiO^2$. In particular, an ssDNA probe 405 may be coupled to nanoelectrodes 407 which are terminated at terminal ends 409. The substrate layer portion 403 may cover a much smaller area than the total surface area of the card 401. In one embodiment, the card 401 may be sized to be conveniently handled by a human user. FIG. 4 further illustrates a device 411 for receiving the card 401. The device 411 may include a docking port 412 that is sized and shaped to receive the card 401. Device 411 may include corresponding terminals 414 for interfacing with terminal ends 409 of the card 401 when the card 401 is docked. The device 411 may include an external circuit 417 for connecting to the card 401. The external circuit 417 may include a power source for applying a potential across the terminal ends 409 of the card 401 and/or a conductance meter. The external circuit 417 may include other components for powering the card 401 or detecting parameters of the card 401.

The described DNA detection system provides for instant identification of a specific DNA marker that may be used for revealing the presence of disease related genes (e.g., cancer and cystic fibrosis), bacterial (e.g., tuberculosis and anthrax) and/or viral (e.g., AIDS and avian flu) components. The described method and system results in substantially enhanced measuring process that enables identification of target genes down to a single molecule level without the need for utilizing any bulky equipment, fancy laboratories, skilled technical personnel, requiring minimal sample preparation and hence ideal medical, environmental and forensic use. Due to high specificity, minimal sample volume and label-free instant detection, the prototype has immense potentiality to be integrated into a microfluidic system for immediate application in the field of medical diagnostics or gene mapping.

The invention claimed is:

1. A method of detecting a single-stranded DNA molecule having a particular gene sequence comprising:
   determining a target strand of DNA having a particular gene sequence;
   preparing a single-stranded template DNA that contains a complementary gene sequence to the target DNA strand;
   coupling the template DNA strand to first ends of two single-walled carbon nanotubes by establishing an amide bond between each of the first ends and the template DNA strand, wherein the combination of the template DNA and the two nanotubes forms a probe;
   applying an electric potential between the second ends of the two nanotubes to form a dielectrophoretic field between the nanotube first ends;
   applying a test solution containing single-stranded DNA to the probe;
   measuring a first conductance of the probe before applying the test solution and measuring a second conductance of the probe a second time after applying the test solution; and
   determining a presence of the target strand of DNA in the test solution, the target DNA having a complementary gene sequence to the template DNA, when the conductance after application of test solution is greater than the conductance before application of test solution by a threshold.

2. The method of claim 1, wherein coupling the template DNA strand to first ends of two single-walled carbon nanotubes comprises applying a solution of template DNA strands to the two carbon nanotubes while applying an electric potential between the second ends of the two nanotubes to form a dielectrophoretic field between the first ends of the nanotubes.

3. The method of claim 1, wherein the electric potential is applied a first time to induce hybridization of the target strand of DNA to the template DNA when the test solution is applied, and applied a second time after the test solution is applied and removed to determine a difference in conductance.

4. The method of claim 1, wherein the electric potential comprises an alternating voltage of 1 Volt peak to peak, at 1 Mhz frequency.

5. The method of claim 1, wherein the test solution is applied for a period of time to allow hybridization of target DNA in the test solution with the template DNA and wherein the test solution is removed with buffer solution before measuring the conductance the second time.

6. The method of claims 5, wherein the period of time is about five minutes.

7. The method of claim 1, wherein preparing a single-stranded template DNA comprises attaching an amine group to each end of the template DNA strand.

8. The method of claim 7, wherein coupling the template DNA strand comprises forming carboxylic acid links on the first ends of the single walled carbon nanotubes, applying an electrophorectic potential between the two nanotube terminals, and using a catalyst to link the amine and carboxlyic acid groups.

9. The method of claim 1, wherein the two nanotubes forming the probe are formed from a single nanotube into which a channel is etched.

10. The method of claim 9, wherein the channel is etched by focused ion-beam etching.

\* \* \* \* \*

UNITED STATES PATENT AND TRADEMARK OFFICE
CERTIFICATE OF CORRECTION

PATENT NO.       : 8,597,492 B2                                             Page 1 of 1
APPLICATION NO. : 12/518841
DATED            : December 3, 2013
INVENTOR(S)      : Choi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1130 days.

Signed and Sealed this
Twenty-second Day of September, 2015

Michelle K. Lee
*Director of the United States Patent and Trademark Office*